United States Patent [19]

Van der Woude

[11] Patent Number: 4,901,374
[45] Date of Patent: Feb. 20, 1990

[54] FACE SHIELD
[75] Inventor: Gerbrig W. Van der Woude, Rock Island, Ill.
[73] Assignee: Prolens
[21] Appl. No.: 184,846
[22] Filed: Apr. 22, 1988
[51] Int. Cl.⁴ .......................... A61F 9/02; A61F 9/06
[52] U.S. Cl. ........................................ 2/453; 2/452; 2/431
[58] Field of Search .................. 2/10, 11, 12, 15, 435, 2/436, 437, 439, 443, 445, 453, 454, 448, 449, 450

[56] References Cited

U.S. PATENT DOCUMENTS

| 1,455,025 | 5/1923 | Kern-Jenny et al. | 2/453 |
| 2,393,955 | 2/1946 | Baratelli et al. | 2/ |
| 2,408,273 | 9/1946 | Sager | 2/ |
| 2,700,765 | 2/1955 | Hoffmaster | 2/443 |
| 2,829,374 | 4/1958 | Malcom, Jr. | |
| 3,016,542 | 1/1962 | Lindblom | 2/453 X |
| 3,016,543 | 1/1962 | Lindblom | 2/453 X |
| 3,214,767 | 11/1965 | Weber | |
| 3,663,959 | 5/1972 | Loubeyre | 2/453 |
| 4,541,125 | 9/1985 | Phillips | 2/453 X |

Primary Examiner—Werner H. Schroeder
Assistant Examiner—Jeanette E. Chapman

[57] ABSTRACT

Disclosed is a shield for protecting the eyes and at least the upper half or more of the face of the wearer and comprises a head-encircling element having a frontal part of relatively rigid material provided with oppositely extending wings for receiving pockets on a headband. The frontal part is configured to conform to the brow of the wearer and a compatibly configured frame is mounted on the frontal part by a transverse hinge. A protective screen of transparent nature depends from the frame in a protective mode and, because of the hinge, can be swung forwardly and upwardly away from and downwardly and rearwardly back to the protective mode. The screen may be removed from the frame and the headband from the frontal part for laundering, sterilizing, etc.

5 Claims, 2 Drawing Sheets

FACE SHIELD

BACKGROUND AND SUMMARY OF THE INVENTION

Despite the abundance of eye and face shields in the art, there is still room for a simple, light-weight and convenient shield especially adapted for use by medical personnel. Prior art shields, designed mainly for use in industry and sports, are found to be too cumbersome in use and over-complicated in design, especially in conditions in which ready separation of the structure is required for such purposes as sterilization, replacement of parts and the like.

According to the present invention an improved shield is provided, having relatively few parts and devoid of fasteners and like attachment structures such as screws, rivets, etc. The few parts are easily separated for ease and convenience in sterilization of the parts and especially by different sterilization procedures compatible with the different materials involved in the make-up of the shield. The transparent screen, for example, is separable from the carrying frame and the fabric or like headband is likewise separable from the frame.

It is a feature of the invention that the hinge for the pivotal mounting of the protective screen is relatively far forward rather than being disposed to the rear as in the prior art. This enables positioning of the screen without leaving wide gaps between the screen and its mounting means. Thus protection is afforded throughout a wide range of angular movement of the screen. A further feature resides in the provision on the frontal part of laterally oppositely extending wings for receiving pockets on the headband, thus enabling removable mounting of the headband. The frontal part further includes a forward ledge or shelf configured to accommodate the brow of the wearer. This shelf adds strength and stability to the fore part of the shield and establishes a base for the hinged mounting of the protective screen. The wings for receiving the headband are formed in such manner as to be flexible for brow conformance, and this is achieved by providing slots or spaces between the wings and ledge, leaving the ledge relatively rigid. The manner of attaching the headband to the wings results in use of the headband material to substantially seal the spaces between the wings and ledge and thus adds to the protection afforded from above the shield.

Further features and advantages will become apparent as a preferred embodiment of the invention is disclosed herein.

DESCRIPTION OF A PREFERRED EMBODIMENT OF THE INVENTION

Figure 4:
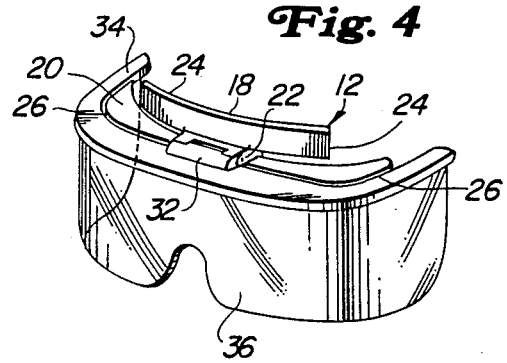
FIG. 4 is a perspective with the headband omitted.

The shield includes a head-encircling element (10) attached to a frontal part (12). The element includes a headband (14) of fabric or like material having provision for adjustment at (16). The frontal part is best seen in FIG. 4 as including a U-shaped strip (18) in the form of a wall configured to accommodate the wearer's forehead or brow. The strip is part of a compatibly configured shelf or ledge portion (20) having a central region or support portion (22) integral with the central region of the brow part (18), it being preferred that the portions (18) and (20) be of fairly rigid material such as any of the well-known plastics suitable for the purpose. The attachment of the portion (18) to only the central region of the shelf or ledge, however, leaves the portion (18) with a pair of laterally outwardly extending wings (24) of relatively flexible nature, a result stemming from the separation of the wings from lateral portions of the ledge by spaces or slots (26).

Figure 5:
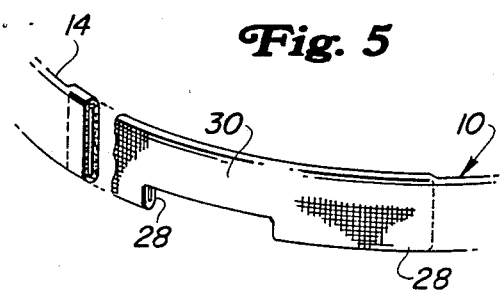
FIG. 5 is a fragmentary perspective showing the pocketed front portion of the headband.
Figure 6:
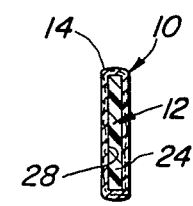
FIG. 6 is an enlarged section on the line 6—6 of FIG. 2.

As best seen in FIG. 5, the front part of the headband (14) is of tubular construction and thus provides laterally oppositely opening pockets (28) for respectively receiving the wings (24). The portion of the band between the pockets, as at (30), is elastic so that, after each pocket is slipped inwardly onto its wing, the elastic portion draws the pockets together to establish the connection. The band is easily stretched oppositely to remove it from the wings for separate laundering, replacement, etc.

Figure 1:
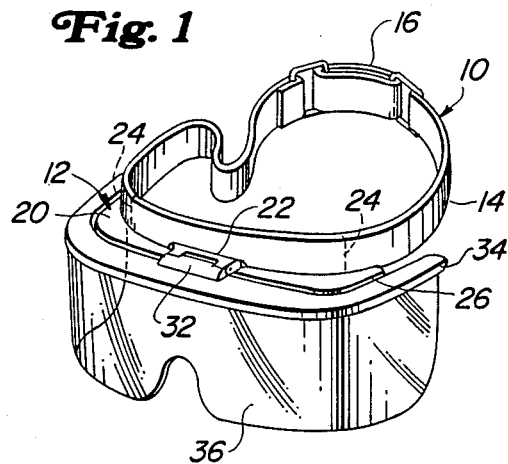
FIG. 1 is a perspective of the shield.
Figure 2:
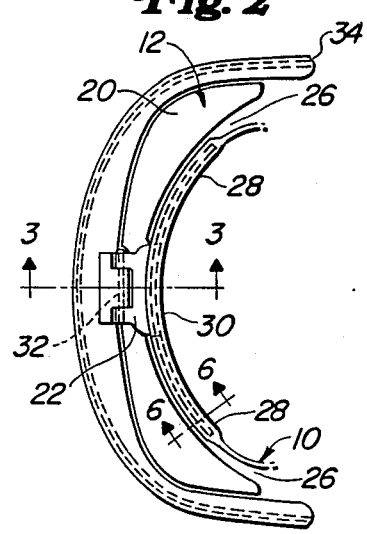
FIG. 2 is a plan view of the structure.
Figure 7:
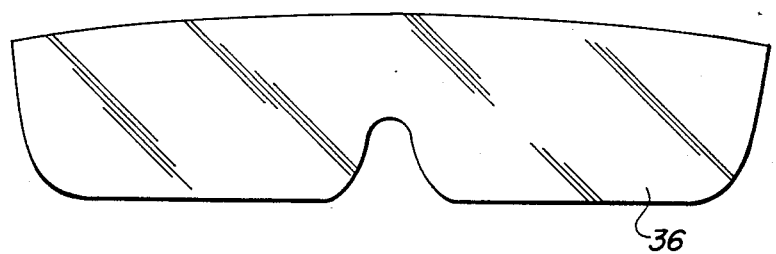
FIG. 7 is a front view of one form of protective screen.
Figure 8:
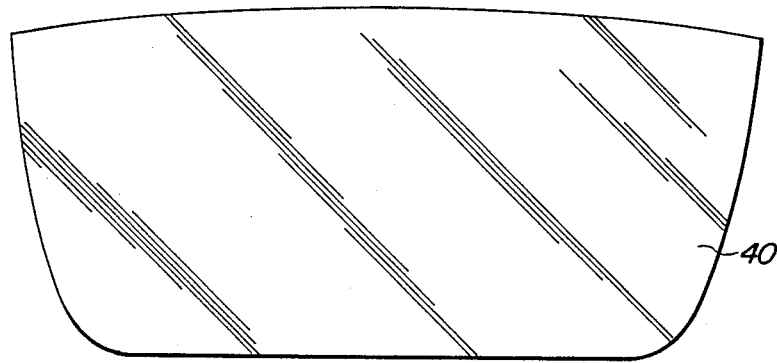
FIG. 8 is a front view of another form of protective screen.

The central portion (22) is of thicker section than the rest of the ledge and thus serves as part of a hinge (32) for the mounting of a U-shaped frame (34) generally horizontally coplanar with the ledge (20) and again configured according to the typical brow or forehead of a person. The hinge provides a transverse horizontal pivot confined generally centrally of the structure where the meeting portions of the frame and ledge are essentially straight. This hinge is disposed frontally for convenience in selective positioning of the frame and its depending protective screen (36), the frame having an underside channel (38) providing screen mounting means into which the upper portion of the screen is tightly but removably received. The screen (36) is shown in flat condition in FIG. 7 and is curved as seen in FIGS. 1, 2 and 4 because it is manually shaped to that configuration when fitted into the frame channel. The material of which the screen is made may be of polycarbonate, for example. During the sterilization process, the screen will be removed from the frame and will return to its flat status. An alternate screen is shown at (40) in FIG. 8, being of greater area than the screen (36), which may be required in certain conditions.

Figure 3:
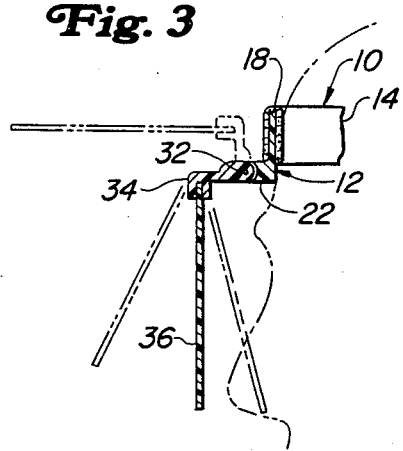
FIG. 3 is a section, on an enlarged scale, taken on the line 3—3 of FIG. 2 and showing in broken lines an outline of the wearer's face and several positions of the shield relative to its full-line protective or normal mode.

As seen in FIG. 3, the "normal" protective mode of the screen may be perceived as shown in full lines. Nevertheless, because of the forward location of the hinge (32), other protective modes may be used, such as swung back toward the face or forwardly away from but still in front of the face, as well as a upward or horizontal model. This is but one of the several features of the shield. Others, as already noted, are the simplicity of the construction, the easy separability of the few parts, the elimination of complicated fasteners, etc. Still other features will become apparent to those versed in the art, as will many alterations in and additions to the embodiment shown, all without departure from the spirit and scope of the invention.

I claim:

1. A face shield, comprising a head-encircling element including a frontal part adapted to fit against the brow of the wearer and having a relatively rigid central support portion, a protective screen positionable in a protective mode in dependent relation to the frontal part and closely ahead of the eyes of the wearer, said screen having an upper edge portion closely proximate to the support portion of the frontal part, and screen-mounting means including a relatively rigid frame disposed closely ahead of the frontal part and of U-shaped configuration as seen from above so as to generally conform to the brow of the wearer, said screen-mounting means further including a hinge on a transverse axis connecting a central region and the frame and the central support portion of the frontal part, the screen being also U-shaped to conform to the frame and the upper edge portion of the screen being removably carried by the frame and said frame further including a downwardly-opening channel configured to conform to the frame and relatively tightly receiving the upper edge portion of the screen, and said shield being initially flat and of flexible material adapted to be manually curved to fit the channel and capable of returning to its flat status when removed from the channel.

2. A face shield, comprising a head-encircling element having a frontal part including an upright arcuate wall having a rear surface adapted to fit against the brow of the wearer and an arcuate, horizontal ledge conforming generally to the wall and projecting forwardly from the wall, said ledge and wall being joined at only their respective regions and the wall having lateral wings extending oppositely from its central region, and spaced respectively from lateral portions of the ledge, said ledge having a central support portion, a relatively rigid frame disposed ahead of the frontal part and of U-shaped configuration as seen from above so as to conform to the arcuate ledge and including a hinge on a transverse axis connecting a central region of the frame to the aforesaid support portion, a protective screen carried by and depending from the frame in a protective mode closely ahead of the eyes of the wearer, and the head-encircling element including a flexible headband having a pair of laterally spaced apart pockets respectively receiving the aforesaid wings.

3. A face shield according to claim 1, in which each pocket extends along the girth of the headband and opens laterally inwardly toward and for receiving its associated wing.

4. A face shield according to claim 3, in which the headband includes an elastic portion connected to and spanning the pockets for drawing the pockets inwardly toward each other and onto the wings.

5. A face shield according to claim 4, in which the headband portions providing the pockets substantially close the spaces between the wings and the ledge.

* * * * *